US008609834B2

(12) United States Patent
Wang

(10) Patent No.: US 8,609,834 B2
(45) Date of Patent: Dec. 17, 2013

(54) METHOD FOR SYNTHESIZING SUCROSE-6-ACETIC ESTER

(75) Inventor: Xiaoqiang Wang, Shenzhen (CN)

(73) Assignee: Shenzhen New Trend Industrial Development Co. Ltd., Shenzhen (CN)

( * ) Notice: Subject to any disclaimer, the term of this patent is extended or adjusted under 35 U.S.C. 154(b) by 1473 days.

(21) Appl. No.: 11/936,960

(22) Filed: Nov. 8, 2007

(65) Prior Publication Data
US 2008/0269478 A1  Oct. 30, 2008

(30) Foreign Application Priority Data

Apr. 25, 2007  (CN) .......................... 2007 1 0074157

(51) Int. Cl.
| C07H 11/00 | (2006.01) |
| C07H 1/00 | (2006.01) |
| C07H 3/00 | (2006.01) |
| C08B 37/00 | (2006.01) |

(52) U.S. Cl.
USPC ........................... 536/115; 536/1.11; 536/124

(58) Field of Classification Search
USPC ......................... 536/1.11, 115, 124
See application file for complete search history.

(56) References Cited

U.S. PATENT DOCUMENTS

| 2,396,201 | A | * | 3/1946 | Ray ................................ 562/869 |
| 5,440,026 | A | | 8/1995 | Khan et al. |
| 5,449,772 | A | | 9/1995 | Sankey |
| 6,939,962 | B2 | | 9/2005 | Clark et al. |

FOREIGN PATENT DOCUMENTS

| CN | 1453285 | 11/2003 |
| CN | 1827628 | 9/2006 |
| EP | 0515145 | 11/1992 |
| GB | 2079749 A | * 1/1982 ............... C07H 3/04 |
| JP | 2211888 | 8/1990 |

OTHER PUBLICATIONS

Kattnig, E., Albert, M. (2004) Counterion-Directed Regioselective Acetylation of Octyl β-D-Glucoside. Organic Letters, vol. 6, No. 6, p. 945-948.*
Tate, B.E., Bartlett, P.D. (1956) The Dimerization of Acetyl Cyanide. The Journal of American Chemical Society, vol. 78, p. 5575-5580.*
"2.2 Recrystallization" [online], [retrieved Dec. 10, 2009]. Published on the internet Sep. 12, 2003. Retrieved from the Internet <http://siggy.chem.ucla.edu/VOH/136/Recrystallization.pdf>.*
Luft, J.R., Wolfley, J.R., Saik, D.I., Nagel, R.M., Lauricella, A.M., Smith, J.L., Thayer, M.H., Veatch, C.K., Snell, E.H., Malkowski, M.G., Detitta, G.T. (2007) Efficient optimization of crystallization conditions by manipulation of drop volume ratio and temperature. Protein Science, vol. 16, No. 4, p. 715-722.*
Nass, K.K. (1994) Rational Solvent Selection for Cooling Crystallizations. Industrial & Engineering Chemistry Reseach, vol. 33, p. 1580-1584.*

* cited by examiner

*Primary Examiner* — Scarlett Goon
(74) *Attorney, Agent, or Firm* — Johnson & Martin, P.A.; James David Johnson

(57) ABSTRACT

The present invention discloses a method of synthesizing sucrose-6-acetic ester, comprising the following steps: adding sucrose into a polar aprotic solvent, and stirring the solvent to dissolve it, then generate a suspension solution of sucrose; adding a acetylation agent acetylnitrile into said suspension solution and stirring the solution; adding water into the aforesaid reaction solution, and then concentrating it to generate a concentrated product; adding a crystalline solvent into the concentrated product, stirring to dissolve it, and depositing for crystallization, then filtering and drying it to get a product of sucrose-6-acetic ester. The benefit of the present invention is that the method of synthesizing sucrose-6-acetic ester has simple operation, mild reaction condition, high selectivity, high yield, and is suitable for industrial production.

8 Claims, No Drawings

METHOD FOR SYNTHESIZING SUCROSE-6-ACETIC ESTER

CROSS-REFERENCE TO RELATED PATENT APPLICATION

This application claims the priority of Chinese patent application No. 200710074157.9, filed Apr. 25, 2007; which is herewith incorporated by reference in its entirety.

FIELD OF THE INVENTION

The present invention relates to a method for organic synthesis, more particularly, to a method for synthesizing a crucial intermediate, i.e. sucrose-6-acetic ester, when preparing sucralose.

BACKGROUND OF THE INVENTION

Sucralose is a product using sucrose as a raw material, in which three hydroxies are selectively substituted with chlorine. It has 600 times sweetness more than a granulated sugar, and the taste is similar to the granulated sugar, and it has the characteristic of great stability in respect of heat and pH. Since 1976, when it was discovered in a cooperated research of UK company Tate & Lyl with a university, it has been introduced and popular in many countries.

The method of synthesizing sucralose mainly comprises two kinds, that is, hologroup protected synthesis and monoesterification, wherein the latter one is more widely used to synthesize sucralose. Therefore synthesis of sucrose-6-acetic ester, which is a crucial intermediate when synthesizing sucralose utilizing the method of monoesterification, is always concerned. U.S. Pat. No. 6,939,962 disclosed a method for synthesizing sucralose, which achieves an ideal result by using acetic anhydride as an acetylation reagent, and under catalysis of organotin, using cyclohexane as an azeotropic dehydration reagent. However, this method has high cost, and the operation is complex and the raw materials are difficult to buy. Moreover, U.S. Pat. No. 5,449,772, European patent EP0515145 also disclosed another method of synthesizing sucrose-6-acetic ester, which get a cyclized intermediate through a reaction of sucrose and Trimethyl orthoacetate, and then the cyclized intermediate is hydrolyzed to generate a composition of sucrose-6-acetic ester and sucrose-4-acetic, and then a portion of sucrose-4-acetic is converted sucrose-6-acetic ester by using tert-butylamine as a converter. This method is simple on operation, and the reaction is mild, but the selectivity of acylation is poor. Moreover, other patents also disclosed the method of synthesizing sucrose-6-acetic ester, such as U.S. Pat. No. 5,440,026 using ketene acetal as a acylating agent, Japanese patent JP2211888 using enzyme catalysis, Chinese patent CN1827628 using electrolytic process and CN1453285 using solid sulphate as a catalyst. All of these methods have the disadvantages of poor selectivity or low conversion rate.

SUMMARY OF THE INVENTION

To overcome the aforementioned disadvantages, the present invention provides a method for synthesizing sucrose-6-acetic ester, including the following steps:

S1: Adding sucrose into a polar aprotic solvent, and stirring the solvent to dissolve it, then generate a suspension solution of sucrose;

S2: Adding an acetylation agent such as acetylnitrile into said suspension solution. and stirring the solution;

S3: Adding water into the reaction solution of step S2, and then concentrating it to generate a concentrated product;

S4: Adding a crystalline solvent into the concentrated product, stirring to dissolve it, and depositing for crystallization, then filtering and drying it to get a product of sucrose-6-acetic ester.

Advantageously, said acetylation agent acetylnitrile is obtained by reaction of diethoxy-phosphoryl cyanide dissolved in acetic acid.

Advantageously, a reaction temperature of diethoxy-phosphoryl cyanide and acetic acid is 25° C.-35° C.

Advantageously, said acetylnitrile obtained by the reaction of diethoxy-phosphoryl and acetic acid, is purified by distillation after the reaction.

Advantageously, in said step S2, a mole proportion of acetylnitrile and sucrose is 0.8:1~3:1.

Advantageously, said polar aprotic solvent is selected from N,N-dimethylfonnamide (DMF), hexamethyl-phosphoric triamide, acetonitrile, or propionitrile.

Advantageously, in said step S2, a reaction temperature of acetylnitrile and sucrose is 20° C.~60° C.

Advantageously, in said step S4, said solvent is a component solvent of water and acetone.

Advantageously, a proportion of water and acetone in said component solvent of water and acetone is 1:3~1:8.

A synthesizing route of the present invention is:

1. Synthesis of acetylnitrile:

$$NC-\overset{O}{\underset{OC_2H_5}{\overset{\|}{P}}}-OC_2H_5 \xrightarrow{CH_3COOH} CH_3\overset{O}{\underset{\|}{C}}CN$$

2. Synthesis of sucrose-6-acetic ester

The benefit of the present invention is that compared with the prior art, the present method for synthesizing sucrose-6-acetic ester is simple on operation, the reaction condition is mild, the selectivity is good (sucrose-6-acetic ester/sucrose-4-acetic.25), the yield is high (.87.) and it is suitable for industrially production.

DETAILED DESCRIPTION OF THE PREFERRED EMBODIMENT

Following are further descriptions of the present invention with detailed embodiments, but the present invention is not limited to the particular embodiment disclosed.

Embodiment 1

Synthesis of acetylnitrile

At the temperature of 30° C., 50 g diethoxy-phosphoryl cyanide is added into 500 ml acetic acid solvent with concentration of 99%, stirred and reacts in the solution for 5 hours. Then ammonia gas is blown into the solution. And then distilled liquid are collected during a decompression distillation of the solution, which is thus the acetylnitrile.

Embodiment 2

Synthesis of sucrose-6-acetic ester 25 g acetylnitrile is added into 500 ml DMF, which contains 100 g dry and shattered sucrose suspending therein. Then the DMF solution is heated to 40° C. and reacted under stirring for 4 hours. After the solution is limpid, it is heated to 50° C., and continues to react for 2 hours. Then the solution is cooled down to room temperature, and then is decompression concentrated to approximate dry after slowly dropping 30 ml water into it. And then 30 ml water is added into the concentrated product, and heated to 65° C. After all the concentrated product is dissolved in the water, it is cooled down to room temperature, and then is slowly added with 150 ml acetone in a manner of drop. Then the resulting solution is deposited for 3 hours at room temperature, and is crystallized. After filtering and vacuum drying the crystal, the product of sucrose-6-acetic ester is obtained, with the weight of 97 g (the content is 98%).

Embodiment 3

Synthesis of sucrose-6-acetic ester 50 g acetylnitrile is added into 500 ml hexamethyl-phosphoric triamide, which contains 100 g dry and shattered sucrose suspending therein. Then the solution is heated to 20° C., reacts under stirring for 4 hours. Then the solution is cooled down to room temperature, and is decompression concentrated to approximate dry after slowly dropping 60 ml water into it. And then 30 ml water is added into the concentrated product, and heated to 65° C. After all the concentrated product is dissolved in the water, it is cooled down to room temperature, and then is slowly added with 100 ml acetone in a manner of drop. Then the resulting solution is deposited for 3 hours at room temperature, and is crystallized. After filtering and vacuum drying the crystal, the product of sucrose-6-acetic ester is obtained, with the weight of 101 g (the content is 97%).

Embodiment 4

Synthesis of sucrose-6-acetic ester 60 g acetylnitrile is added into 500 ml acetonitrile, or propionitrile, which contains 100 g dry and shattered sucrose suspending therein. Then the solution is heated to 60° C., reacts under stirring for 2 hours. Then the solution is cooled down to room temperature, and is decompression concentrated to approximate dry after slowly dropping 100 ml water into it. And then 30 ml water is added into the concentrated product, and heated to 65° C. After all the concentrated product is dissolved in the water, it is cooled down to room temperature, and then is slowly added with 200 ml acetone in a manner of drop. Then the resulting solution is deposited for 3 hours at room temperature, and is crystallized. After filtering and vacuum drying the crystal, the product of sucrose-6-acetic ester is obtained, with the weight of 100 g (the content is 95%).

I claim:

1. A method for synthesizing sucrose-6-acetic ester, consisting of the following steps:
    (a) adding sucrose into a polar aprotic solvent and stirring the solvent to generate a suspension solution of sucrose, wherein said polar aprotic solvent is selected from the group consisting of: N,N-dimethylformamide, hexamethyl-phosphoric triamide, acetonitrile, and propionitrile;
    (b) adding acetylnitrile into said suspension solution and stirring the solution at a reaction temperature of acetylnitrile and sucrose of 20° C.-60° C.;
    (c) adding water into the reaction solution of step (b) and then concentrating it to generate a concentrated product; and
    (d) adding crystallization solvent into the concentrated product, stirring to dissolve it, and depositing for crystallization, then filtering and drying it to get a product of sucrose-6-acetic ester.

2. The method for synthesizing sucrose-6-acetic ester as in claim 1, wherein said acetylnitrile is obtained by reaction of diethoxy-phosphoryl cyanide dissolved in acetic acid.

3. The method for synthesizing sucrose-6-acetic ester as in claim 2, wherein a reaction temperature of diethoxy-phosphoryl cyanide and acetic acid is 25° C.-35° C.

4. The method for synthesizing sucrose-6-acetic ester as in claim 2 or 3, wherein said acetylnitrile obtained by the reaction of diethoxy-phosphoryl and acetic acid, is purified by distillation after the reaction.

5. The method for synthesizing sucrose-6-acetic ester as in claim 1, wherein a mole proportion of acetylnitrile and sucrose is 0.8:1-3:1.

6. The method for synthesizing sucrose-6-acetic ester as in claim 1, wherein in said step (d), said solvent is a component solvent of water and acetone.

7. The method for synthesizing sucrose-6-acetic ester as in claim 6, wherein a proportion of water and acetone in said component solvent of water and acetone is 1:3-1:8.

8. The method for synthesizing sucrose-6-acetic ester as in claim 1 or 6, wherein the temperature for crystallization is 10° C.-30° C.

* * * * *